US009370645B2

(12) United States Patent
Rohl et al.

(10) Patent No.: US 9,370,645 B2
(45) Date of Patent: Jun. 21, 2016

(54) DELIVERY DEVICES AND RELATED METHODS OF USE

(71) Applicant: Boston Scientific Scimed, Inc., Maple Grove, MN (US)

(72) Inventors: James Rohl, Prescott, WI (US); Mary Byron, Roseville, MN (US); Joel Eggert, Plymouth, MN (US); Sandra Nagale, Westford, MA (US); Mark Boden, Harrisville, RI (US); David Lehse, Oakdale, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 14/211,838

(22) Filed: Mar. 14, 2014

(65) Prior Publication Data

US 2014/0276610 A1 Sep. 18, 2014

Related U.S. Application Data

(60) Provisional application No. 61/798,618, filed on Mar. 15, 2013.

(51) Int. Cl.
*A61M 29/00* (2006.01)
*A61M 25/10* (2013.01)
*A61M 37/00* (2006.01)

(52) U.S. Cl.
CPC ..... *A61M 25/1011* (2013.01); *A61M 2025/105* (2013.01); *A61M 2025/1013* (2013.01); *A61M 2037/0023* (2013.01)

(58) Field of Classification Search
CPC ............ A61M 25/10; A61M 25/1011; A61M 25/1002; A61M 25/0084; A61M 25/0074; A61M 2025/0084; A61M 2025/1013; A61M 2025/0036; A61M 2025/0087; A61M 2025/1086; A61M 2025/105; A61M 2025/0086; A61M 2037/0023
USPC ................ 604/101.02, 103.01, 503, 506, 509
See application file for complete search history.

(56) References Cited

U.S. PATENT DOCUMENTS

| | | | |
|---|---|---|---|
| 6,692,490 B1 | 2/2004 | Edwards | |
| 2007/0282184 A1 | 12/2007 | Roberts | |
| 2010/0152704 A1* | 6/2010 | Lee et al. | 604/517 |
| 2010/0198139 A1* | 8/2010 | Glickman | 604/30 |
| 2010/0256594 A1* | 10/2010 | Kimmell et al. | 604/506 |
| 2010/0268191 A1* | 10/2010 | Trudel et al. | 604/509 |
| 2011/0166516 A1* | 7/2011 | Orr | 604/103.01 |
| 2013/0018281 A1 | 1/2013 | Nagale et al. | |
| 2013/0090640 A1 | 4/2013 | Nagale et al. | |
| 2013/0090648 A1 | 4/2013 | Nagale et al. | |

FOREIGN PATENT DOCUMENTS

WO WO 2012/083155 A2 6/2012
WO WO 2012083155 A2 * 6/2012

* cited by examiner

*Primary Examiner* — Theodore Stigell
*Assistant Examiner* — Tiffany Legette
(74) *Attorney, Agent, or Firm* — Bookoff McAndrews, PLLC (57) ABSTRACT

A medical device including an outer balloon, an inner balloon, and at least one delivery unit is disclosed. The outer balloon defines a first internal cavity that remains in fluid communication with a first inflation lumen. The inner balloon is disposed within the first internal cavity, and defines a second internal cavity that is in fluid communication with a second inflation lumen. Each delivery unit includes at least one needle configured to pierce a tissue and at least one reservoir containing a material. Further, inflation of the outer balloon or the inner balloon is structured and arranged to deliver the material into the tissue through the needle lumen.

15 Claims, 7 Drawing Sheets

DELIVERY DEVICES AND RELATED METHODS OF USE

CROSS-REFERENCE TO RELATED APPLICATION

This application claims the benefit of U.S. Provisional Application No. 61/798,618, filed Mar. 15, 2013, the disclosure of which is incorporated herein by reference in its entirety.

FIELD OF THE DISCLOSURE

This disclosure relates generally to devices and methods for delivery of substances into the body of a subject. In addition, it relates to using multi-site injection techniques and/or injecting fluid at a pre-determined depth.

BACKGROUND

Urinary incontinence is a significant health concern worldwide. For example, overactive bladder (OAB) is a chronic urological condition characterized by pain, urinary frequency, urgency with or without urinary incontinence, and varying degrees of sexual dysfunction. The quality of life of OAB patients can be comparable to that of end stage renal failure. OAB affects about 1 million people in the U.S. alone, with 90% of them women.

Recent studies concerning OAB have suggested that there is no known cure for OAB, and so current treatments are targeted to relieve symptoms. Current treatments for overactive bladder include medication, diet modification, programs in bladder training, electrical stimulation, and surgery. A major challenge in treating OAB with a medication is delivery of the medication to sites within the bladder.

Improved delivery devices and methods, as alternatives to, or in conjunction with, the current treatment options are needed. The present disclosure is directed to overcoming the problems above and other shortcomings in the art.

SUMMARY OF THE DISCLOSURE

In one aspect of the disclosure, a medical device including an outer balloon, an inner balloon, and at least one delivery unit is disclosed. The outer balloon may have a first internal cavity configured to be in fluid communication with a first inflation lumen. The inner balloon may dispose within the first internal cavity and may define a second internal cavity configured to be in fluid communication with a second inflation lumen. The delivery unit may include at least one needle capable of piercing a tissue and at least one reservoir containing a material. In an implementation, inflation of the at least one of the outer balloon or the inner balloon is structured and arranged to deliver at least some portion of the material into the tissue.

Another aspect of the disclosure is directed to a medical device having an outer balloon, an inner balloon, and at least one delivery unit including a needle and a reservoir. Each outer and inner balloon includes an internal cavity fluidly connected to an individual inflation lumen. Further, the inner balloon may be disposed within the internal cavity of the outer balloon. The needle includes a tip, an aperture along the needle length, and a needle lumen. The needle is further configured to move between a first position and a second position such that the needle may pierce the target tissue in the second position. The reservoir contains a material. In an implementation, inflation of at least one of the outer balloon or the inner balloon causes the needle to deliver the at least some portion of the material into the tissue through the needle lumen.

In yet another aspect of the disclosure a method for delivering a medicament to bladder tissue is disclosed. The method includes introducing a catheter shaft including a medical device in a collapsed state. The medical device includes an outer balloon an inner balloon, and at least one delivery unit. The outer balloon may have a first internal cavity configured to be in fluid communication with a first inflation lumen. The inner balloon may dispose within the first internal cavity and may define a second internal cavity configured to be in fluid communication with a second inflation lumen. Further, the delivery unit may include at least one needle capable of piercing a tissue and at least one reservoir containing a material, which remains in fluid communication with a needle lumen. Returning to the method of delivery, the catheter shaft is advanced into a body space. The outer or inner balloons may be inflated such that the at least one needle moves form a first position to a second position. In contrast to the first position, the needle in second position pierces the tissue. Eventually, at least a portion of the material is delivered to the tissue through the needle.

Additional objects and advantages of the claimed disclosure will be set forth in part in the description which follows, and in part will be apparent from the description, or may be learned by practice of the disclosure.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference is now made in detail to embodiments of the present disclosure, examples of which are illustrated in the accompanying drawings. Wherever possible, the same reference numbers will be used throughout the drawings to refer to the same or like parts.

Overview

The present disclosure is generally directed to a medical device employing a material (for example, medicament) that may be delivered at a controlled rate at a pre-determined depth to multiple sites within a tissue, for example, within a bladder wall. Embodiments may include an outer balloon defining an internal cavity, which may include one or more delivery units. Each delivery unit may include at least one needle configured to pierce the target tissue. The needles may provide fluid communication to the tissue site with at least one reservoir containing the medicament. Inflation of the outer balloon may allow the outer balloon to contact the inner bladder wall. In some instances, partial inflation of the outer balloon may allow the needle to come in contact with the inner bladder wall. Further, inflation of the outer balloon may then pierce the inner bladder wall. In addition, the medical device may include an inner balloon disposed within the internal cavity of the outer balloon. Inflation of the inner balloon may flatten the reservoir and deliver the medicament, contained within the reservoir into the bladder tissue through the needles.

Embodiments of the present disclosure include by way of example a medical device and/or method adapted to deliver a medicament within the urinary bladder wall. However, it is contemplated that use of the device is not limited to the urinary bladder or to the urinary tract; and the device may be applied in any organ, lumen, or cavity. Examples of organs or lumens may include a nasal cavity, blood vessels, throat, vocal cord/box, trachea and bronchi, esophagus, stomach, colon, duodenum, bile and pancreatic ducts, ear, heart, sphincters (e.g., sphincter of oddi), valves (e.g., heart valves or pulmonary valves), uterus, vagina, or the like.

In the following sections, various exemplary structural and functional features of medical devices will be described. It will be understood that the medical devices may include an outer balloon and an inner balloon for delivering the medicament at the target tissue. Those skilled in the art will appreciate that the medical device may include additional balloons and/or other inflatable structures without departing from the scope of the present disclosure.

It may be contemplated that the components and the configurations of the medical device are just exemplary and thus not limiting the scope and spirit of the present disclosure. Therefore, any suitable component and the configuration of the medical device may be included based on the application.

EXEMPLARY EMBODIMENTS

Figure 1:
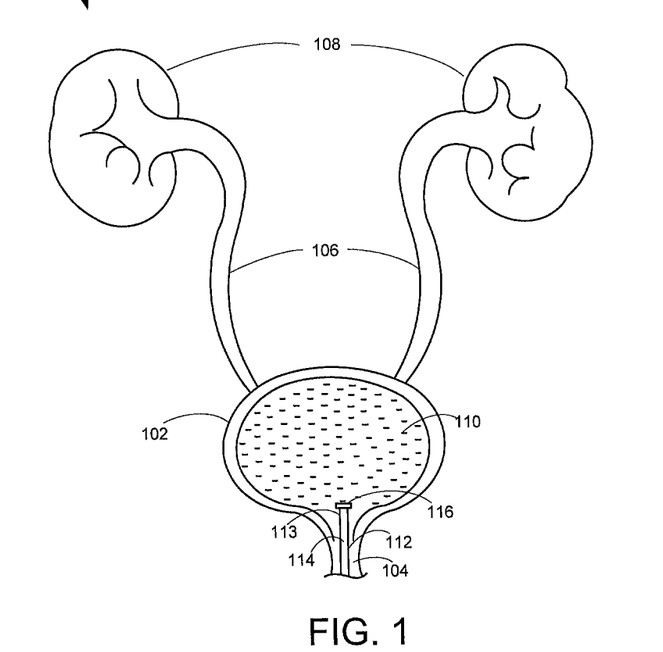
FIG. 1 is a schematic view of a catheter disposed in a urinary tract.

FIG. 1 is a schematic view of an exemplary urinary tract 100 of an individual. The urinary tract 100 includes among other things a bladder 102 that is in fluid communication with a urethra 104. Bodily fluid 110 travels down from the kidneys 108 to the bladder 102 via ureters 106. Muscles (not shown) in the ureter walls tighten and relax to force the bodily fluid 110 downward away from the kidneys 108. Bladder 102 generally accumulates the bodily fluid 110, for example, urine, that is then discharged from the body through urethra 104.

As illustrated, a drain catheter 112 may be employed to evacuate the bladder 102 filled with the bodily fluid 110. The drain catheter 112 may be slidingly positioned within the urinary tract, and in particular, within the bladder 104. Drain catheter 112 generally includes a drain catheter body 114 having a distal draining end 113 and a proximal draining end (not shown) that remains external to the patient's body. Drain catheter 112 is generally inserted such that an opening 116 to the drain lumen is positioned just inside the bladder 102. Bodily fluid 110 may be drained out of the bladder 102 by suction or other methods.

Figure 2A:
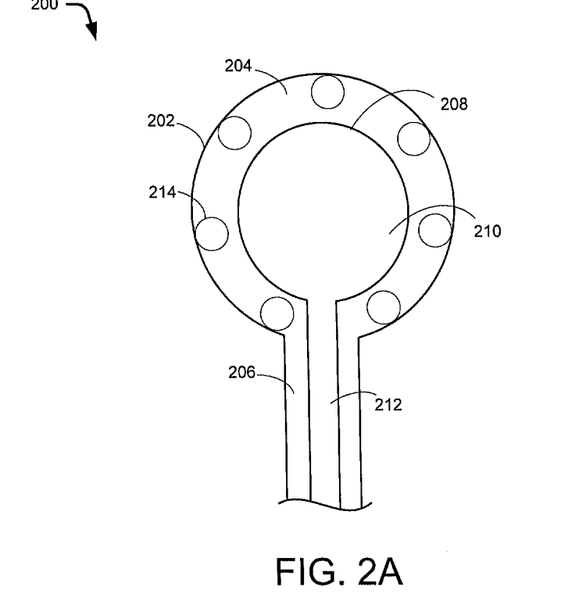
FIG. 2A is a schematic view of an exemplary medical device according to embodiments of the present disclosure.

Turning now to FIG. 2A, an exemplary medical device 200 for treating bodily tissue is depicted. In general, the device 200 may be adapted to deliver a material (not shown) to the bladder 102 (as shown in FIG. 1) of a patient. More specifically, the medical device 200 may be employed to deliver a medicament at a pre-determined tissue depth such as a sub-mucosal tissue layer (not shown) into the wall of the bladder 102. To accomplish this, the medical device 200 may be configured to transition between a fully expanded state and a collapsed state (see FIG. 2B), which will be discussed below.

The medical device 200 may include an outer balloon 202 defining a first internal cavity 204 that may remain in fluid communication with a first inflation lumen 206 as shown in FIG. 2A. Further, the medical device may include an inner balloon 208, which may be disposed within the first internal cavity 204. As alluded to above, the outer and inner balloons 202 and 208 may be configured to transition between the fully expanded state (where either of the outer or the inner balloons are inflated to deliver a material into the bladder tissue) and the collapsed state (where both the outer and inner balloons are deflated to have a compressed state). Such transition may be may be done using any known techniques, for example, inflation and deflation of the two balloons 202 and 208, respectively.

The outer balloon 202 may substantially encompass at least a portion of the inner balloon 208. The inner balloon 208 may include a second internal cavity 210 adapted to be in fluid communication with a second inflation lumen 212. The first and the second inflation lumens 206 and 212 may allow entry of an inflation fluid (not shown) such as a gas, a liquid, or the like within the first and the second internal cavities 204 and 210, respectively. The flow of the inflation fluid into the two inflation lumens 206 and 212 may operate to inflate the first and second internal cavity 204 and 210. Therefore, the inflation fluid and the two inflation lumens 206 and 212 may operate in tandem with each other to inflate the first internal cavity 204 and the second internal cavity 210, respectively. It is contemplated that suitable inflation fluids may include, but not limited to, gas, liquid, or the like.

Further, the two internal cavities 204 and 210 may be deflated to collapse the medical device 200 for various purposes. For instance, the medical device 200 may be collapsed for easy insertion or retraction through the narrow passage such as the urethra 104. To accomplish this, a suitable method such as, but not limited to, suction may be employed. In some embodiments, a suitable medical device such as, but not limited to, a nozzle may be introduced into the two inflation lumens 206 and 212 to inflate and/or deflate the inner and the outer balloons 208 and 202.

In some embodiments, the outer balloon 202 and the inner balloon 208 may have a generally spherical shape, for example—a round balloon having a circular cross-section. However, those skilled in the art will appreciate that the two balloons 202 and 208 may take any suitable shapes and/or cross-sections, which may be selected based on the organ where it is being introduced. Such cross-sections may include, but are not limited to, triangular, polygonal, oval, irregular, or the like. In some embodiments, the shape of the inner balloon 208 can generally correspond to that of the outer balloon 202 or may be of a different shape depending on the application.

Materials employed to manufacture the outer balloon 202 and the inner balloon 208 may include any suitable biocompatible material. In certain instances, the material of the outer balloon may include a soft, flexible polymer such as silicone, for example. Other polymers providing flexibility to the outer balloon 202 may also be contemplated. In contrast, the inner balloon 208 can have a smooth outer surface and can be made of a harder polymer, for example, SIBS. Alternatively, an alloy, a composite, a metal, or the like may be employed to manufacture the two balloon 202 and 208. For instance, a self-expandable material such as Nitinol™, or the like may be employed. This is presented as an example, and, is not intended to limit the scope of the present disclosure.

Further, the medical device 200 may include at least one delivery unit 214. Each delivery unit 214 may include at least one piercing member (for example, a needle), capable of piercing an inner bladder tissue wall (not shown in FIG. 2A). The piercing member or needle can be fluidly connected to at least one reservoir containing the medicament. The delivery unit 214 may be placed within the first internal cavity 204 of the outer balloon 202, as shown in FIG. 2A. In contrast, the delivery unit 214 may also be located at any suitable position such as, but not limited to, on an exterior surface (not shown) of the outer balloon 202, within the second internal cavity 210 of the inner balloon 208, and so forth. Further discussion of the delivery units is provided below with reference to FIGS. 3A and 3B.

FIGS. 2B, 2C, 2D, and 2E illustrate exemplary stages of the deployment of the medical device 200 of FIG. 2A within the bladder 102 according to embodiments. As will be discussed in subsequent figures, the medical device may be configured to transition between the collapsed configuration (see FIG. 2B), a first expanded configuration (see FIG. 2C), an intermediate expanded configuration (see FIG. 2D), and the fully expanded configuration delivering a medicament (see FIG. 2E).

Figure 2B:
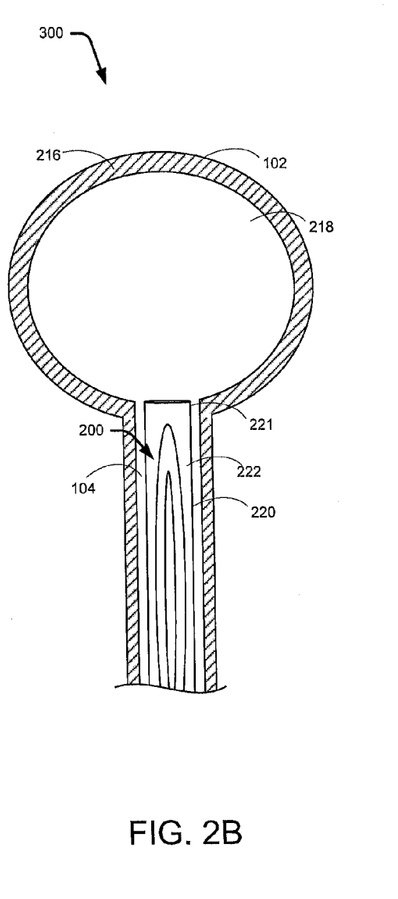
FIG. 2B is a schematic view of the medical device of FIG. 2A disposed in the urinary tract in a collapsed configuration.

As shown in FIG. 2B, the medical device 200 may be introduced into the body and advanced into the bladder 102 via a catheter 220 traversing the urethra 104. The catheter 220 may include a lumen 222 extending between a distal end 221 and a proximal end (not shown) that remains external to the patient's body. Catheter lumen 222 may substantially encompass the inflatable medical device 200 of FIG. 2A in a collapsed state.

The collapsed state may include the outer balloon 202 (as shown in FIG. 2A) and inner balloon 208 (as shown in FIG. 2A) of the medical device 200 in a deflated configuration. To accomplish this, the medical device 200 may be deflated, which may typically include deflation of the first and second internal cavities 204 and 210 (as shown in FIG. 2A). Suitable deflation methods may include, but are not limited to, suction, or the like. According to an example, suction of the first and second internal cavities 204 and 210 (as shown in FIG. 2A) may compress the outer and inner balloons 202 and 208 (as shown in FIG. 2A), thereby deflating the overall medical device 200.

Figure 2C:
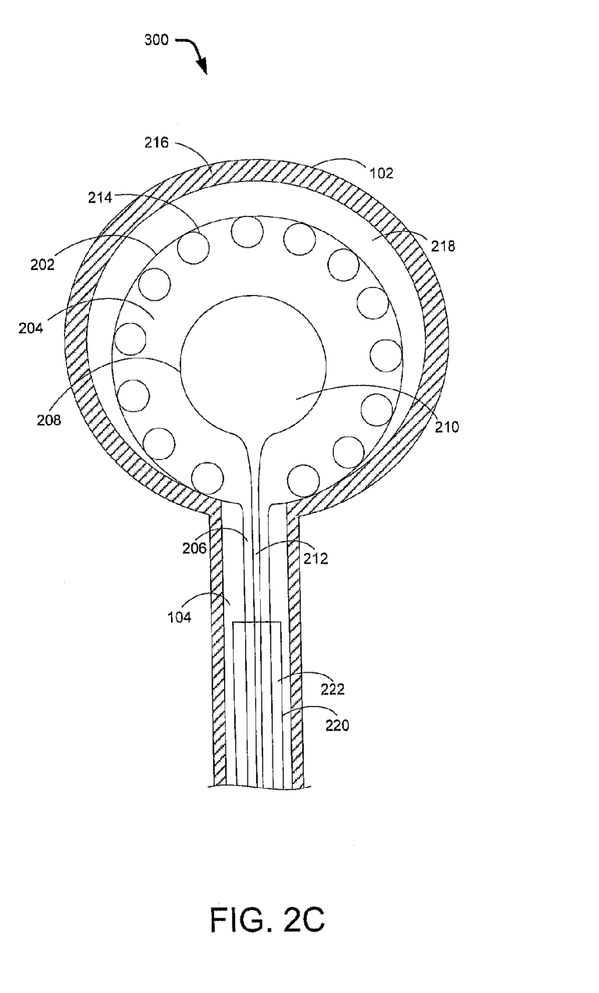
FIG. 2C is a schematic view of the medical device of FIG. 2A disposed in the urinary tract in a first expanded configuration.

Further, the medical device 200 may be advanced within the bladder 102 using a device such as the catheter 220. After the medical device 200 enters the bladder 102, it may transition from the collapsed configuration of FIG. 2B to the first expanded state, as shown in FIG. 2C. An inflation fluid (not shown) may be flowed into the first inflation lumen 206 to inflate the outer balloon 202 partially. In some embodiments, the second internal cavity 212 of the inner balloon 208 may also be partially inflated by delivering an inflation fluid through the second inflation lumen 212.

Figure 2D:
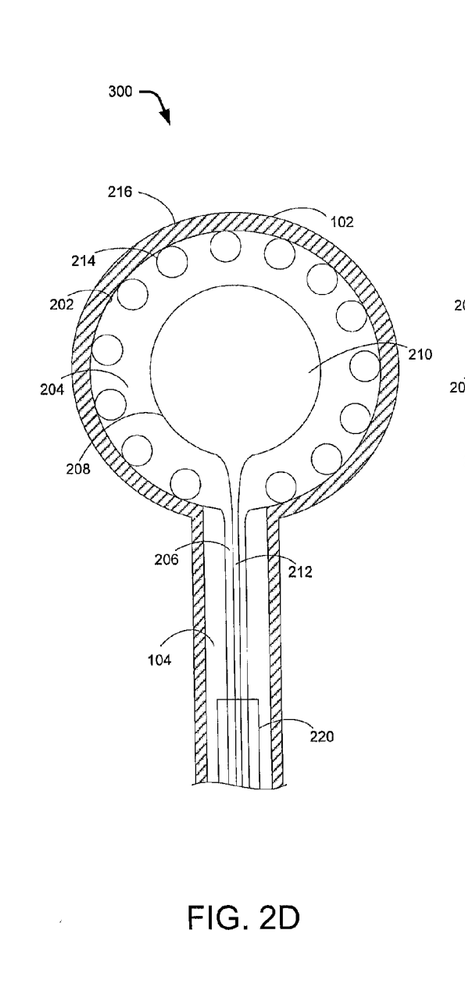
FIG. 2D is a schematic view of the medical device of FIG. 2A disposed in the urinary tract in one expanded configuration where the outer balloon is in contact with the bladder wall.

Following advancing of the outer balloon 202 within a bladder cavity 218, the medical device may be shifted to the intermediate expanded configuration (as shown in FIG. 2D). In such a configuration, the outer balloon can be inflated to come in contact with the inner bladder wall 216 and further inflation of the outer balloon 202 may allow the needles (not shown in FIG. 2A-2E) of the delivery units 214 to pierce the bladder wall 216 to a pre-determined extent or depth.

Figure 2E:
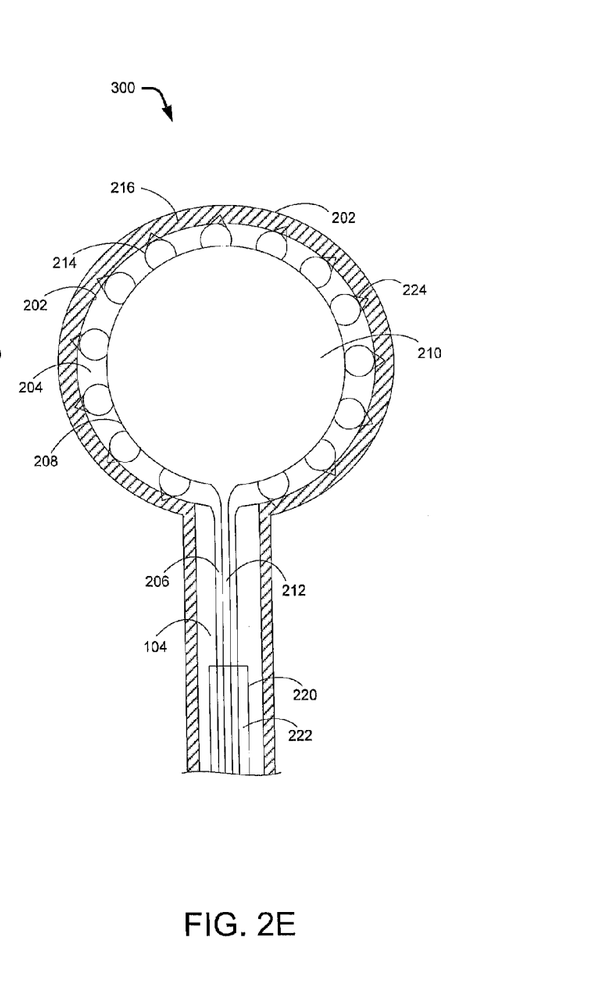
FIG. 2E is a schematic view of the medical device of FIG. 2A disposed in the urinary tract delivering a medicament into the bladder tissue.

Once the needles pierce the bladder wall 216, the inner balloon 208 may be inflated to come in contact with the delivery units 214 (as shown in FIG. 2E). Further inflation of the inner balloon 208 may physically compress parts of the delivery units 214, e.g., the reservoir attached adjacent the proximal end of each needle (see FIGS. 3A, 3B, for example), which may deliver the medicament to or into the bladder wall 216 through each needle. As shown, the medicament may be delivered to a pre-determined depth 224 of the bladder wall 216, and depicted as the fully expanded configuration of the medical device 200 (FIG. 2E). Further details about the delivery of medicament within the bladder wall 216 will be discussed below.

Figure 3A:
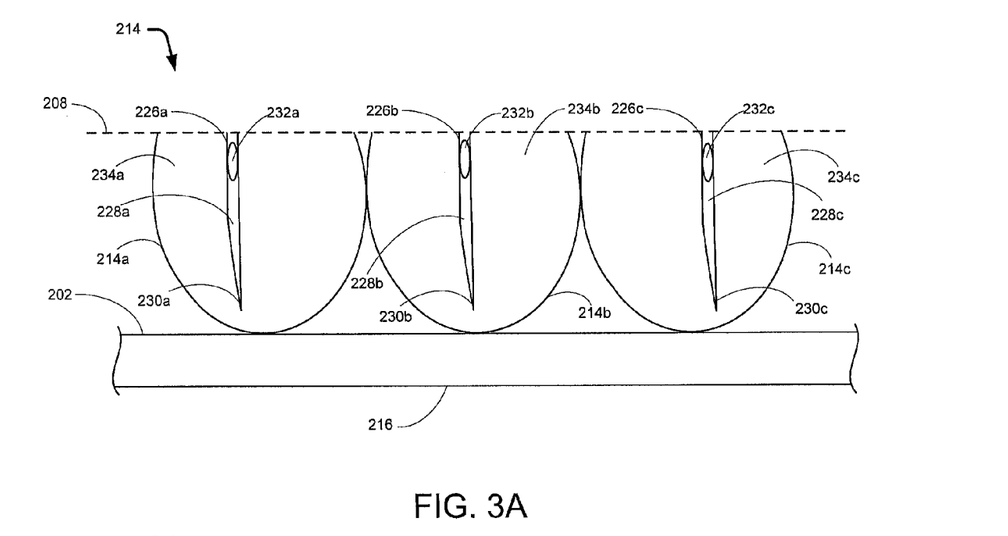
FIG. 3A is a schematic view of an array of delivery units of FIGS. 2A-2E.

FIG. 3A is a schematic view of an array of delivery units 214 for use with the medical devices of FIGS. 2A-2E. Here, the delivery units 214a, 214b, and 214c may rest along the inner surface of the outer balloon 202, which in turn is placed along the inner surface of the bladder wall 216. In the example shown here, the delivery units 214 may be capsule-shaped, having a rounded cross-section. Those skilled in the art will appreciate that any suitable cross-section such as circular, rectangular, oval, irregular, or the like may also be contemplated. Although, only three delivery units are shown, it may be contemplated that any suitable number of delivery units 214 (as shown in FIGS. 2A, 2C-2E) may be employed. The delivery units 214 are depicted in a circumferential array in FIG. 2C-2E, but it is understood that any arrangement of delivery units 214 is within the scope of this disclosure. For example, the deliver units 214 can be arranged in multiple circumferential arrays, targeted arrays for a particular location within an organ, and/or arrays tailored to the shape of the organ the medical device 200 is being introduced into.

In addition, each delivery unit 214a, 214b, and 214c may include a piercing member such as a needle 226a, 226b, and 226c, respectively. The needles 226a, 226b, and 226c may be elongated with a sharp needle tip 230a, 230b, and 230c, which are capable of piercing a tissue surface such as the bladder wall 216. Those skilled in the art will appreciate that any suitable piercing member may be contemplated without departing from the spirit and scope of the present disclosure. Suitable examples may include, but are not limited to, blades, cutters, or the like.

In the example shown here, the needles 226a, 226b and 226c are hollow each defining a needle lumen 228a, 228b, and 228c, respectively. In addition, each needle 226a, 226b and 226c may include an aperture 232a, 232b, and 232c disposed along a portion of length of the needles. Each aperture 232a, 232b, and 232c may provide a fluid connection between the needle lumen 228a, 228b, and 228c and a respective reservoir 234a, 234b, and 234c. Further, an external force such as pressure may be applied on the reservoirs 234a, 234b, and 234c, which may deliver the medicament (not shown) contained within the reservoirs to the needle lumens 228a, 228b, and 228c via respective needle apertures 232a, 232b, and 232c. Further application of pressure on the reservoirs 234a, 234b, and 234c may allow delivery of the medicament (not shown) held within the needle lumens 228a, 228b, and 228c to the target tissue.

It is contemplated that the needles 226a, 226b, and 226c may be open at the needle tip 230a, 230b, and 230c and include the apertures 232a, 232b, and 232c enabling delivery of the medicament (not shown) at a certain depth in the bladder wall 216. In such instances, the medicament (not shown) may be delivered to the tissue only when the aperture is in fluid communication with the reservoir. Alternative configurations of the needles 226 may include, but are not limited to, slotted needles, or the like.

Needles 226 may be made of any suitable biocompatible material having enough stiffness to pierce a tissue. Suitable examples may include, but are not limited to, metals, polymer, composite, or the like. In certain instances, alloys such as Nitinol™ may also be contemplated. Those skilled in the art will appreciate that any suitable material allowing the desired function may be employed without departing from the scope and spirit of the present disclosure. For example, the needles 226 may be made from a material that allows for folding or bending to assist in the medical device 200 It is also understood that the needles 226 can be oriented at any non-normal angle with respect to the tissue that will provide for pierce the tissue. For example, needles may be oriented at a 45 degree angle with respect to the tissue.

It is contemplated that the medicament may include any suitable therapeutic agents having therapeutic properties such as healing a tissue, generating biochemical signals in vivo, or the like. Examples of the medicament may include a drug such as peptides, proteins, or the like. In particular, the medicament may also include treatment fluids such as Botox, stem cells, or the like. It is to be noted that one skilled in the art will be able to include any medicament providing the therapy for urinary tract disorders such as overactive bladder, for example. The medicament may also include diagnostic and/ or prophylactic agents. These are presented as examples, and, are not intended to limit the scope of the present disclosure.

Further, the medicament and/or drug may include a hydrogel. Hydrogels include a swellable polymeric biomaterial, which has substantially been adapted as a carrier for a drug. A hydrogel carrier can be formulated in a variety of physical forms including, but not limited to, micro-particles, coatings, films, or the like. According to an example, the drug may be encapsuled within the hydrogel carrier, which may then be delivered to the body tissue treating an ailment. In such instances, the hydrogel carrier may protect the encapsulated drug from any hostile environment (for example, unfavorable pH, temperature, or the like) in vivo. In addition, the porosity of the hydrogel carrier contributes in controlling the drug release rate within the tissue. For instance, highly porous hydrogel carrier may allow fast release of the drug in comparison to a less porous carrier. In addition to using hydrogel as a carrier, the drug may also be mixed with a hydrogel solution in a desired ratio, which may then be injected within the body tissue.

Figure 3B:
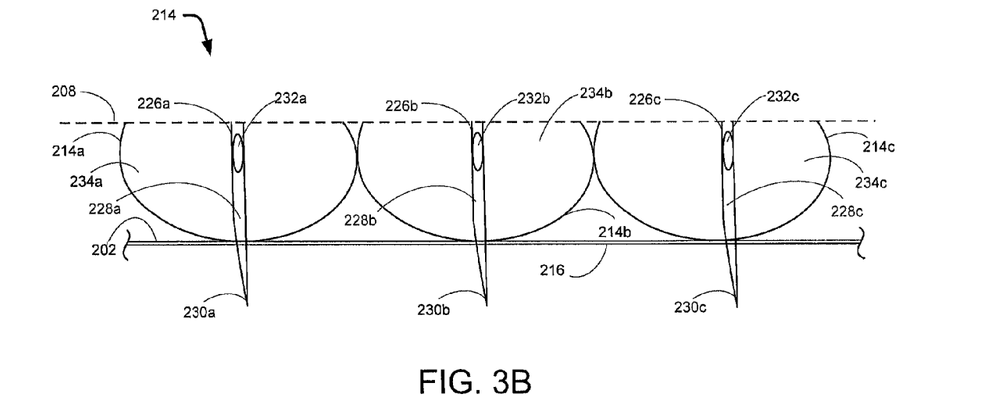
FIG. 3B is a schematic view of the delivery units of FIG. 3A with the needles piercing the bladder wall.

FIG. 3B is a schematic view of the exemplary delivery units 214 of FIG. 3A with the needles 226a, 226b, and 226c piercing the bladder wall 216. As previously discussed, the outer balloon 202 may be fully inflated to come in contact with the bladder wall 216 (see FIG. 3A), and further inflation of the outer balloon 202 may allow the needles 226a, 226b, ad 226c to pierce the bladder wall 216.

In the illustrated embodiment, the delivery units 214 are in partially compressed state such that the needle tips 230a, 230b, and 230c pierces the bladder wall 216. Once, the needles 216a, 216b, ad 216c reaches a pre-determined depth within the bladder tissue, the inner balloon 208 may be inflated to compress the reservoirs 234a, 234b, and 234c such that the medicament may enter the needle lumens 228a, 228b, and 228c. Further, inflation of the inner balloon 208 may allow delivery of the medicament through the needle tip 230a, 230b, and 230c.

While not explicitly shown, inflation of the inner balloon 208 compresses the reservoirs 234a, 234b, and 234c facilitating delivery of the medicament into the needle lumens 228a, 228b, and 228c through the apertures 232a, 232b, and 232c. Further inflation of the inner balloon 208 may deliver the medicament into the bladder tissue. In addition, delivery rate of the medicament may be controlled by controlling the inflation rate and pressure of the inner balloon 208. In addition, the formulation of the medicament, which may include hydrogel may also affect the medicament delivery rate into the bladder wall 216. Other factors that may affect the delivery rate include the diameter of the needle lumens 228a, 228b, and 228c, the profile of the needle tips 230a, 230b, and 230c, or the like. Additional factors may also affect the medicament delivery rate.

It is also contemplated that the medical device 200 may be configured to inflate and/or deflate into various shapes designed by varying the material properties and wall thicknesses. Thus, the material employed to manufacture the medical device 200 may employ either single or a group of materials to achieve the desired inflation/deflation and drug flow conditions. In contrast, a single material with various durometers may also be used to manufacture the medical device 200.

Figure 4A:
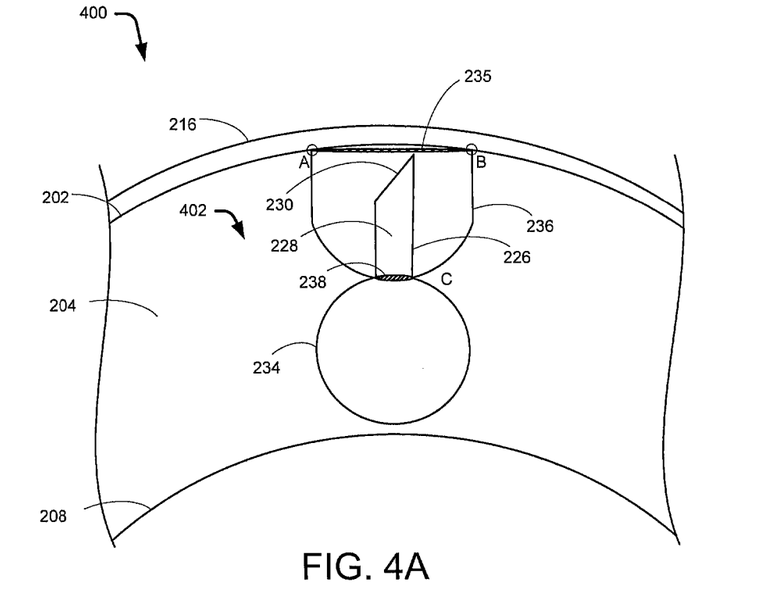
FIG. 4A is a schematic view of an exemplary medical device disposed in the urinary tract according to embodiments of the present disclosure.

FIG. 4A is a schematic view of an exemplary medical device 400, according to embodiments of the present disclosure. The device 400 may include a delivery unit 402 disposed within the first internal cavity 204 of the outer balloon 202. As discussed previously, the delivery unit 402 includes the needle 226 coupled to the reservoir 234 such that the needle lumen 228 may remain in fluid communication with the reservoir 234.

It is contemplated that the delivery unit 402 may be embedded within the first internal cavity 204 at an intersection C. The intersection C may include a membrane 238 configured to couple the needle 226 to the reservoir 234, while being disposed in between the needle 226 and the reservoir 234. Those skilled in the art will appreciate that the membrane 238 may include any suitable structures including, but not limited to, pouch, or the like.

According to an embodiment, the membrane 238 may be configured and arranged to restrict entry of the medicament contained within the reservoir 234 to the needle lumen 228. Further, the membrane 238 may be made from any suitable flexible material, which may allow entry of the medicament into the needle lumen on application of an external pressure on the reservoir. Examples may include polymer, composite, alloys, or the like. In some embodiment, the membrane 238 may have flexibility depending on a variety of factors including: 1) sufficient strength to avoid inadvertent entry of medicament in the needle lumen, 2) compression force required to burst the membrane 238 to deliver the medicament contained within the reservoir 234 to the needle lumen 228, and so forth.

In addition, the medical device 400 may include a pocket 236 such that the needle may rest inside it. As shown, the pocket 236 may have a cup-shaped configuration having a semi-circular cross-section. It is noted that other suitable shapes and cross-sections of the pocket may also be contemplated. Further, the semi-circular pocket 236 may define an outer ring 235 that may be attached to the outer balloon at two ends A and B of the outer ring 235.

In the illustrated embodiment, the needle 226 may rest within the pocket 236 such that the needle tip 230 may remain under the outer ring 235 of the pocket 236. This configuration may avoid any inadvertent puncture of the surrounding tissue by the needle tip 230, while deploying the medical device 400 inside a body cavity. Once the device 400 is placed at a target region i.e. adjacent the bladder 102, the outer balloon 202 may be inflated. Inflation of the outer balloon 202 may stretch the pocket 236 such that the outer ring 235 may be stretched along the AB line. As a result, the depth of the pocket 236 may decrease. Further inflation of the outer balloon 202 may stretch the pocket 236 to flatten it, thus forcing the needle to puncture into the bladder 102 through outer balloon 202 (as shown in FIG. 4B).

Figure 4B:
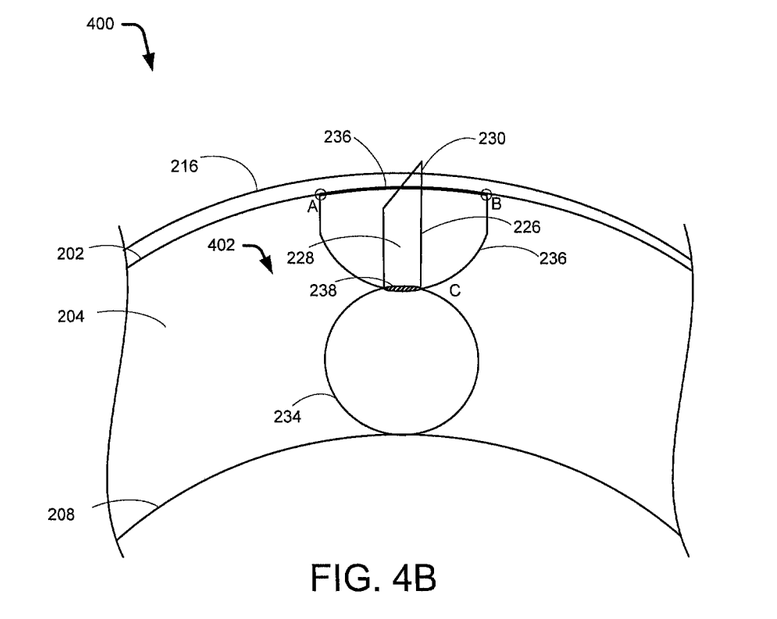
FIG. 4B is a schematic view of the medical device of FIG. 4A in one expanded configuration where the needle of the delivery unit pierces the bladder wall according to embodiments of the present disclosure.

Once the needle 226 is placed within the bladder wall 216, the inner balloon 208 may be inflated such that it contacts the reservoir 234 as shown in FIG. 4B. Further inflation of the inner balloon 208 may compress the reservoir 234, which may rupture the membrane 238. This may allow delivery of the medicament, and hydrogel, contained within the reservoir 234 into the needle lumen 228, which on further inflation of the inner balloon 208 may deliver the medicament to the bladder 102.

In one embodiment, hydrogel may be disposed within the membrane 238. In such instances, the compression of reservoir 234 during inflation of the inner balloon 208 may burst the membrane 238, which may deliver a combination of hydrogel and the medicament (contained in the reservoir 234) to the bladder 102.

In an embodiment, the pocket 236 and the membrane 238 may be made from an easy to puncture biocompatible material, which may include a polymer, for example. Those skilled in the art will appreciate that any suitable biocompatible material may be employed to manufacture the pocket 236 and the membrane 238, without departing from the scope and the spirit of the present disclosure.

Figure 5A:
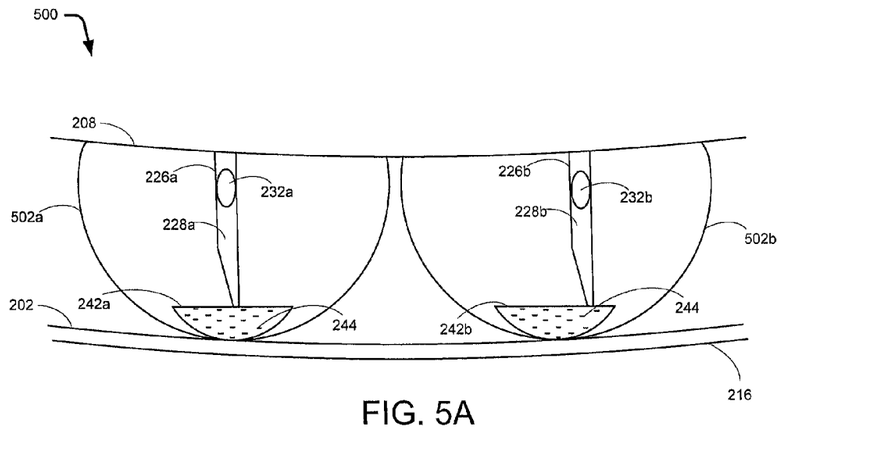
FIGS. 5A, 5B, and 5C are schematic views of alternate embodiments of medical device configurations according to embodiments of the preset disclosure.
Figure 5B:
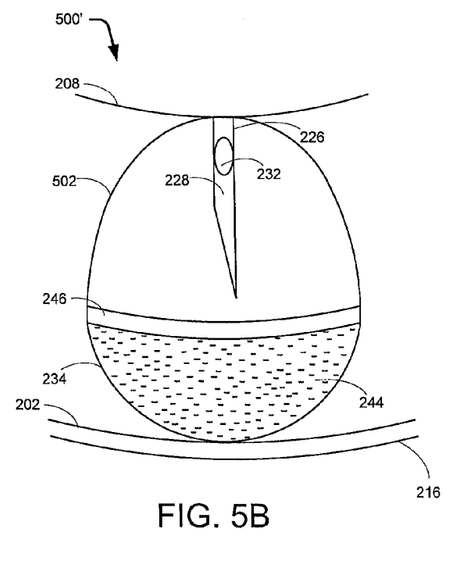
Figure 5C:
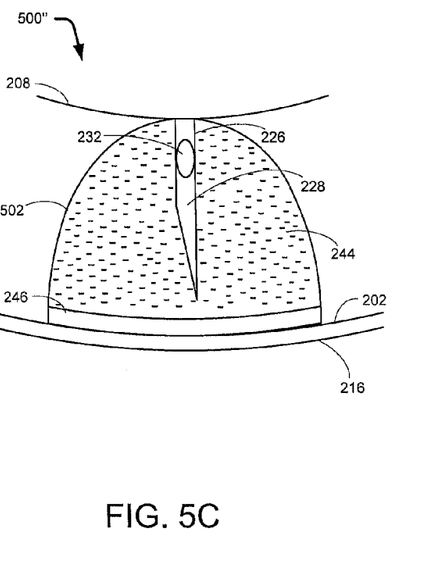

Turning now to FIGS. 5A, 5B, and 5C, schematic views of exemplary medical devices 500, 500' and 500" are depicted. For instance, the embodiment of FIG. 5A may include an array of delivery units having individual delivery units 502a and 502b disposed within the outer balloon 202. Each delivery unit 502a and 502b may include a needle 226a and 226b having its distal needle tip 230a and 230b (as shown in FIGS. 3A-3B) in communication with a pouch 242a and 242b, respectively. Each pouch 242a and 242b may further include the medicament 244.

It is contemplated that each pouch 242a and 242b may be made up of an easy-to-puncture material such that the needle tip may be capable of puncturing the pouches. Exemplary materials may include a biocompatible polymer, an alloy, or the like. These are just examples and are not intended to limit the scope of the disclosure.

As shown, the inner balloon 208 may be inflated to compress the delivery units 502a and 502b, which may allow the needles 226a and 226b to puncture the pouches 242a and 242b such as to deliver the medicament 244 to the target tissue. In contrast to the previous embodiments, inflation of the inner balloon 208 is configured to place the needles 226a and 226b within the bladder wall 216 followed by delivery of medicament 244 into the tissue. Once the needles 226a and 226b punctures the bladder wall 216 at a pre-determined depth, further inflation of the inner balloon 208 delivers the medicament 244 contained within the pouch 242a and 242b to the tissue. In an implementation, the needle apertures 232a and 232b positioned inside the pouches 242a and 242b dictates the depth to which the needles 226a and 226b will pierce the target tissue.

FIG. 5B shows a medical device 500' according to another embodiment of the present disclosure. Here, the delivery unit 502 includes the reservoir 234 containing the medicament 244 and the needle 226. Unlike the embodiment shown in FIG. 5A, the delivery unit 502 includes a flexible membrane 246, which may be positioned to separate the needle 226 from the reservoir 234. Moreover, the delivery unit 502 may be disposed in the cavity of the outer balloon 202. In an implementation, the inner balloon 208 may be inflated to compress the delivery unit 502 and more particularly the needle 226 such as to puncture the membrane 246 and thus the reservoir 246. Further inflation of the inner balloon 208 may puncture the outer balloon 202 and deliver the medicament 244 contained within the reservoir 246 to the target tissue. The needle apertures 232 while positioned inside the reservoir 234 may allow delivery of the medicament 244 to the bladder tissue.

In contrast, FIG. 5C shows a medical device 500" that includes both the needle 226 and the medicament 244 disposed within the delivery unit 502. It is contemplated that there will be no requirement for a separate reservoir in this embodiment. Further, the delivery unit 502 may include the membrane 246 structured and arranged to prevent any inadvertent puncture of the outer balloon 202 through the needle 226. Inflation of the inner balloon 208 balloon may pierce the membrane 246 and thus the outer balloon 202, thereby delivering the medicament 244 to the target tissue. As inflation of the inner balloon 208 facilitates both positioning of the needle 226 and delivery of the medicament 244 to the target tissue, it may be contemplated that the delivery unit 500" allows continuous delivery of the medicament 244 to the targeted tissue, based on the rate at which the inner balloon 208 is inflated.

Although a single aperture 232 is shown in embodiments 5A-5C, it may be contemplated that the needle 226 may include two or more apertures 232 and/or perforations, which may allow delivery of a large quantity of the medicament 244 to the tissue.

A further embodiment of the medical device will be described with reference to FIGS. 6 and 7. In some embodiments, the medical device 700 (as shown in FIG. 7) includes one or more deliver units 600 each having a protective tubing network, which will be discussed in detail in conjunction with FIG. 6. According to an example, the protective tubing network may avoid any inadvertent puncture of the surrounding tissue, while the needle 226 passes though a body cavity. In addition, the protective tubing network may be configured and arranged to deliver the medicament through the needle, as needed.

Figure 6:
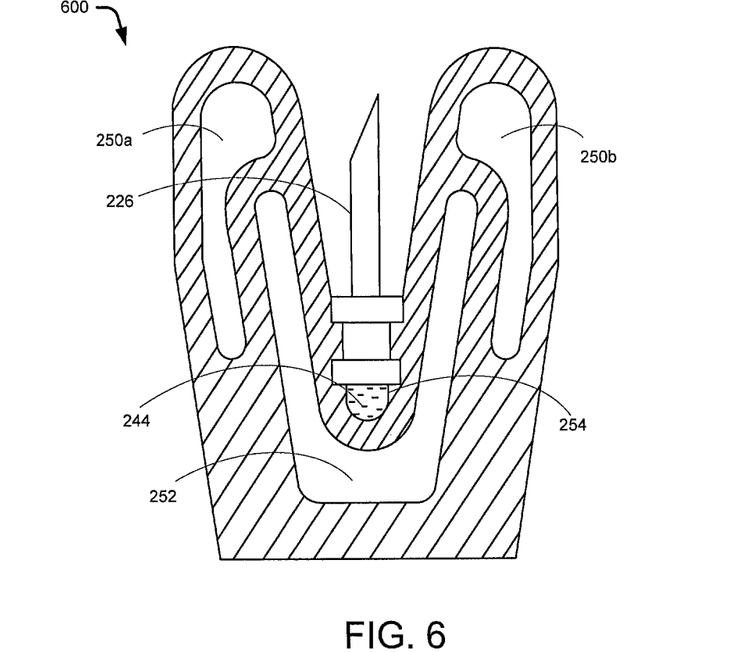
FIG. 6 is a schematic view of an exemplary delivery unit according to embodiments of the present disclosure.
Figure 7:
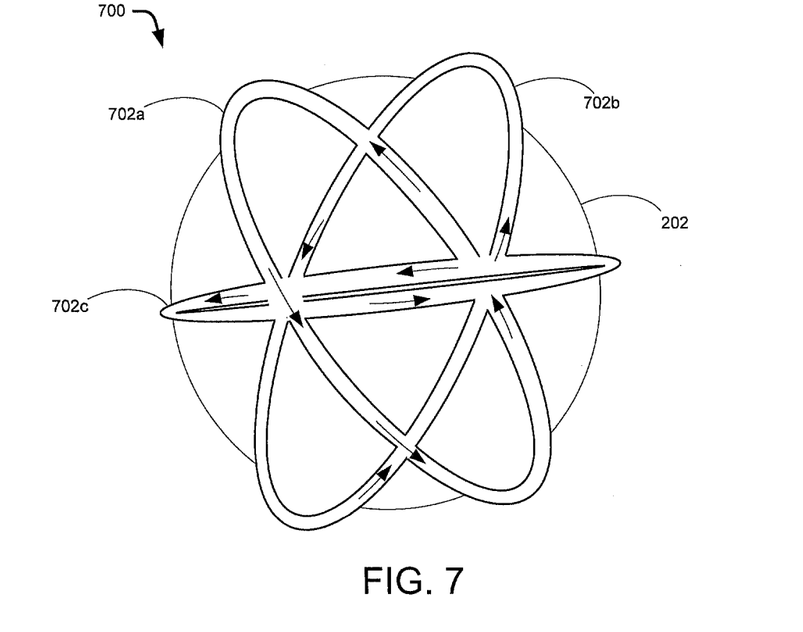
FIG. 7 is a schematic view of an exemplary medical device with multiple delivery units according to embodiments of the present disclosure.

FIG. 6 is a schematic cross-sectional view of another embodiment of a delivery unit 600. The delivery unit 600 includes a needle 226 attached to a reservoir 254 containing the medicament 244. In addition, the delivery unit 600 includes a protective tubing network having lumens for changing the shape of the delivery unit 600. These lumens include needle protector lumens 250a and 250b and a needle deployment lumen 252, which may extend lengthwise through the exemplary conduit. The delivery unit 600 may each be configured to transition between a closed configuration and an open configuration. In the closed configuration (as shown in FIG. 6), the needle protector lumens 250a and 250b and the needle deployment lumen 252 are configured to protect the needle, while being disposed on either sides. However, in the open configuration, the the needle protector lumens 250a and 250b and the needle deployment lumen 252 may be extended to allow the needle to come out. An inflation fluid such as a gas, saline, or the like may be employed to pressurize the needle protector lumens 250a and 250b and the needle deployment lumen 252 to transition between the open and closed configurations. Although not shown, mechanical pressure such as expansion of the inner balloon may also be employed to allow transition of delivery unit 600, and thus the lumens (250a, 250b and 252) from the closed configuration to the open configuration.

The needle protector lumens 250a and 250b may protect the needle 226 from piercing the surrounding tissue while the device is being deployed to the site. For example, the needle-protector lumens 250a and 250b may be inflated using the inflation fluid, which may extend beyond and protect the needle 226 during insertion through the catheter 220 (as shown in FIG. 2B).

Once the device has been deployed at the site, the needle-protector lumens 250a and 250b may be deflated and the needle deployment lumen 252 may be inflated (with air or saline or therapeutic drug), forcing the needle 226 into the tissue, thus delivering the medicament 244, contained in the reservoir 254, through a medicament delivery lumen of the needle.

FIG. 7 shows a medical device 700 in accordance with another embodiment of the present disclosure. The medical device 700 may include one or more conduits 702a, 702b, and 702c attached to an external surface of an outer balloon 202. Each conduit 702a, 702b, and 702c may include a plurality of delivery units 600 (as shown in FIG. 6) disposed thereon. A plurality of conduits running lengthwise through the conduits 702a, 702b, and 702c may carry inflation fluid such as a gas or a liquid, and the flow of fluid in the various lumens can be manipulated to change the shape of the delivery units 600 (as shown in FIG. 6).

Although only three conduits 702a, 702b, and 702c are shown, those skilled in the art will appreciate that any number of conduits may be used based on the application. Similarly, the number of delivery units disposed within the conduits may also vary. Further, the conduits 702a, 702b, and 702c may extend around the outer balloon 202 in any suitable manner. According to an example, the configuration of conduits may vary such that the diameter of the conduits may vary along their length.

The illustrated embodiment may also allow multiple medicaments to be delivered through the multi-site delivery units on continuous bases, as may be controlled by a physician. To accomplish this, one or more reservoirs 254 of one or more delivery units 600 may be filled with different medicaments 244. In addition, the lumens may be inflated and/or deflated in a suitable manner such as to deliver either of the drug or the medicament 244 to the target tissue. Alternatively, both the drug and the medicament 244 may be delivered to the target tissue at once.

In addition, the medical device illustrated in embodiments of the present disclosure may be manufactured using a variety of manufacturing methods. Examples may include, but are not limited to, stamping, press rolling, soldering, brazing, molding, or the like. Further, suitable materials employed to manufacture the device may include any suitable biocompatible material such as metals including, stainless steel, aluminum, titanium, polymers, composites, or the like. The manufacturing methods and materials are presented here as just examples, and hence, are not intended to limit the scope of the present disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A medical device comprising:
   an outer balloon having a first internal cavity in fluid communication with a first inflation lumen;
   an inner balloon disposed within the first internal cavity, said inner balloon defining a second internal cavity in fluid communication with a second inflation lumen;
   a pocket disposed within the first internal cavity, the pocket including an outer member attached to an inner wall of the outer balloon; and
   at least one delivery unit disposed within the first internal cavity, the at least one delivery unit including:
      at least one needle having a needle lumen, the at least one needle being configured to pierce tissue, rest within the pocket, and be positioned to pass through the outer member; and
      at least one reservoir containing a material;
   wherein inflation of at least one of the outer balloon or the inner balloon is configured to facilitate delivery of at least a portion of the material into the tissue through the needle lumen, wherein inflation of the outer balloon causes the at least one needle to be disposed along the inner wall of the outer balloon.

2. The medical device of claim 1, wherein inflation of the inner balloon compresses the at least one reservoir such that the material contained within the at least one reservoir is delivered into the needle lumen.

3. The medical device of claim 1, wherein inflation of the inner balloon ruptures the at least one reservoir to release the material for delivery to the tissue.

4. The medical device of claim 1, wherein the material includes a medicament capable of treating an overactive bladder.

5. The medical device of claim 4, wherein the material further includes hydrogel facilitating controlled-release of the medicament into the tissue.

6. The medical device of claim 1, wherein the pocket is cup-shaped, and the outer member is attached to the inner wall of the outer balloon at two ends.

7. The medical device of claim 6, wherein inflation of the outer balloon stretches the outer member along its two ends to deploy the at least one needle into the tissue while piercing the outer balloon.

8. The medical device of claim 1, wherein the at least one needle is separated from the at least one reservoir by a membrane configured to restrict the entry of the material contained within the at least one reservoir into the needle lumen.

9. The medical device of claim 8, wherein the inflation of the inner balloon compresses the at least one reservoir to burst the membrane, and further inflation of the inner balloon delivers the material contained within the at least one reservoir into the tissue through the at least one needle.

10. The medical device of claim 1, wherein the material and the at least one needle are disposed within the first internal cavity and inflation of the inner balloon causes the at least one needle to pierce the outer balloon and deliver the material into the tissue.

11. A medical device comprising: an outer balloon and an inner balloon each having an internal cavity fluidly connected to a respective inflation lumen, the inner balloon being further disposed within the internal cavity of the outer balloon; an outer member disposed between the outer balloon and the inner balloon; and at least one delivery unit including: a needle having a tip and a needle lumen, the needle being configured to move between a first position and a second position, wherein the outer member is disposed radially between the tip of the needle and the outer balloon when the needle is in the first position; and a reservoir containing a material; wherein inflation of at least one of the outer balloon or the inner balloon facilitates the delivery of at least a portion of the material into the tissue through the needle lumen, and wherein inflation of the outer balloon causes the at least one needle to be disposed along an inner wall of the outer balloon.

12. The medical device of claim 11, wherein the needle in the second position corresponds to a tissue depth position, and wherein the needle in the second position communicates material into the tissue.

13. A method for delivering a medicament to bladder tissue, the method comprising:
 introducing a catheter shaft including a medical device in a collapsed state, the medical device including:
  an outer balloon having a first internal cavity in fluid communication with a first inflation lumen;
  an inner balloon disposed within the first internal cavity, said inner balloon defining a second internal cavity in fluid communication with a second inflation lumen; and
  at least one delivery unit embedded radially within the first internal cavity and including:
   at least one needle being capable of piercing a tissue; and
   at least one reservoir containing a material;
 advancing the catheter shaft into a body space;
 inflating at least one of the outer or inner balloons such that the at least one needle moves from a first position, wherein the at least one needle does not pierce tissue, to a second position, wherein the at least one needle pierces tissue; and
 delivering at least a portion of the material to the tissue through the at least one needle;
 wherein the at least one needle is configured to rest within a cup-shaped pocket located in the first internal cavity, the pocket including an outer member attached to an inner surface of the outer balloon at two ends, and wherein in the second position, the at least one needle pierces the outer member and the outer balloon.

14. The medical device of claim 11, wherein the at least one delivery unit is embedded in the internal cavity of the outer balloon, the needle is configured to rest within a cup-shaped pocket located in the internal cavity of the outer balloon, the cup-shaped pocket including the outer member, which is attached to an inner surface of the outer balloon at two ends, and the needle is positioned to pass through the outer member.

15. The method of claim 13, wherein inflating at least one of the outer or inner balloons includes inflating the outer balloon causing the at least one needle to be disposed along an inner wall of the outer balloon.

* * * * *